(12) United States Patent
Paolitto et al.

(10) Patent No.: US 8,932,344 B2
(45) Date of Patent: Jan. 13, 2015

(54) AORTIC CONDUIT CONFIGURED WITH TERMINAL ENDS HAVING NEOSINUSES OF VALSALVA

(75) Inventors: Anthony Paolitto, St. Leonard (CA); Valerio Velentini, Montreal (CA)

(73) Assignee: Coroneo, Inc., Montreal, Quebec (CA)

( * ) Notice: Subject to any disclaimer, the term of this patent is extended or adjusted under 35 U.S.C. 154(b) by 262 days.

(21) Appl. No.: 13/643,231

(22) PCT Filed: Apr. 29, 2011

(86) PCT No.: PCT/CA2011/000496
§ 371 (c)(1),
(2), (4) Date: Oct. 24, 2012

(87) PCT Pub. No.: WO2011/134070
PCT Pub. Date: Nov. 3, 2011

(65) Prior Publication Data
US 2013/0046379 A1   Feb. 21, 2013

Related U.S. Application Data

(60) Provisional application No. 61/282,957, filed on Apr. 29, 2010.

(51) Int. Cl.
*A61F 2/06* (2013.01)
*A61F 2/24* (2006.01)

(52) U.S. Cl.
CPC ............ *A61F 2/2412* (2013.01); *A61F 2/06* (2013.01); *A61F 2250/0062* (2013.01)
USPC ......... 623/1.31; 623/1.26; 623/1.24; 623/1.3; 623/2.1

(58) Field of Classification Search
USPC ............... 623/1.24, 1.26, 1.3, 1.31, 2.1, 2.13, 623/2.14, 2.15, 2.16, 2.17, 2.18, 2.19
See application file for complete search history.

(56) References Cited

U.S. PATENT DOCUMENTS

| 5,139,515 A | 8/1992 | Robicsek |
| 6,352,554 B2 | 3/2002 | De Paulis |

(Continued)

FOREIGN PATENT DOCUMENTS

EP   0955019 A2   11/1999

OTHER PUBLICATIONS

Canadian Intellectual Property Office, International Search Report and Written Opinion in PCT/CA2011/000496, Aug. 8, 2011.

(Continued)

*Primary Examiner* — David Isabella
*Assistant Examiner* — Suba Ganesan
(74) *Attorney, Agent, or Firm* — Wood, Herron & Evans, L.L.P.

(57) ABSTRACT

A prosthetic aortic conduit (1) for use during surgery on the aorta of a patient. The conduit includes an elongate tubular portion (10) extending along a longitudinal axis (11) between a first conduit terminal end (12) and a second conduit terminal end (13). The first conduit terminal end (12) is configured with two substantially U-shaped tongues (21, 22) extending away from the tubular portion (10) generally along the longitudinal axis (11). Each of the tongues (21, 22) is appropriately sized to together collectively approximate the shape of the scalloped bicuspid valve annulus. The second conduit terminal end (13) is configured with three substantially U-shaped tongues (31, 32, 33) extending away from the tubular portion (10) generally along the longitudinal axis (11). Each of the tongues (31, 32, 33) is appropriately sized to together collectively approximate the shape of the scalloped tricuspid valve annulus.

2 Claims, 10 Drawing Sheets

(56) References Cited

U.S. PATENT DOCUMENTS

| | | |
|---|---|---|
| 6,544,285 B1 * | 4/2003 | Thubrikar et al. ........... 623/2.12 |
| 7,018,404 B2 | 3/2006 | Holmberg et al. |
| 7,309,461 B2 | 12/2007 | Kujawski et al. |
| 7,431,733 B2 | 10/2008 | Knight |
| 2004/0260390 A1 | 12/2004 | Sarac et al. |
| 2005/0234546 A1 | 10/2005 | Nugent et al. |
| 2008/0082161 A1 * | 4/2008 | Woo ............................. 623/1.26 |

OTHER PUBLICATIONS

The International Bureau of WIPO, International Preliminary Report on Patentability in PCT/CA2011/000496, Nov. 8, 2012.

* cited by examiner

AORTIC CONDUIT CONFIGURED WITH TERMINAL ENDS HAVING NEOSINUSES OF VALSALVA

The application claims the benefits of U.S. Provisional Patent Application Ser. No. 61/282,957, filed Apr. 29, 2010, the disclosure of which is hereby incorporated by reference herein.

FIELD OF THE INVENTION

The present invention relates to the field of cardiac or vascular surgery, and more specifically to the field of aortic conduits or vascular grafts used in reconstructive surgery of the aorta or the aortic valve.

BACKGROUND OF THE INVENTION

The mammalian heart is an organ made up of four muscular chambers that function together to pump blood throughout the body. Each of the four chambers has an associated downstream one-way valve made up of movable, coapting leaflets or cusps which cooperate to prevent the backward flow of blood, or regurgitation, into their respective chambers. Two such heart valves, the aortic and pulmonary valves, also commonly known as the semilunar valves, are characterized by three leaflets or cusps 91. The aortic valve leaflets 91 are attached within the aortic root 90, usually to a tri-scalloped or triple scalloped line of collagenous, fibrous tissue generally referred to as the valve annulus 92. As such, a three-pointed crown-like structure serves to support the aortic valve cusps or leaflets 91. The U-shaped convex lower edges of each leaflet are attached to, and suspended from, the base 97 of the aortic root 90, with the upper free edges or margins 93 of each leaflet being free to move and project into the lumen of the aorta 99. Two adjacent leaflets approach one another at one of the three points of said crown-like structure to define a commissure 95 of the aortic valve. Behind each leaflet 91, the aortic vessel wall bulges outward, forming a pouch-like dilatation known as the sinus of Valsalva 98. In the region located slightly above the level of the commissures 95, the aortic root 90 creating the sinuses of Valsalva 98 merges into the substantially tubular portion of the ascending aorta 99 at a substantially planar transition zone commonly known as the sinotubular junction (STJ) 100. The aortic root 90 houses the aortic valve structures and generally includes the portion of the native aortic conduit extending from the left ventricular outflow tract (LVOT) to the portion of ascending aorta 99 slightly above the sinotubular junction (STJ). Typically, aortic root reconstructions or interventions usually involve the aortic valve, while ascending aorta interventions usually exclude the aortic valve and involve the native aortic conduit located generally downstream of the sinotubular junction. In some patients, one or two of the native valve cusps may be congenitally fused and a bicuspid or, more rarely, a unicuspid aortic valve may present.

Aortic root dilation is one of the most common causes of aortic valve incompetence in North America. Prevalence of surgical corrections for this pathology has increased considerably during the last two decades. There are a variety of surgical corrections (for example the Reimplantation technique popularized by David, or the Remodelling technique popularized by Yacoub) that have been developed over the years to surgically repair an aortic valve or reconstruct the aortic root portion of the ascending aorta. In most surgeries, especially conservative aortic valve surgery which restores valve competence in regurgitant aortic valves having occurred from a dilatation of the aortic root or a retraction of valve cusps, surgeons must replace a portion of the patient's native aorta which is dilated, aneurysmal or pre-aneurysmal with a prosthetic vascular conduit. Typically, the native sinuses of Valsalva and a portion of the ascending aorta are resected leaving behind a scalloped native aortic root 89. Said resected aortic tissue is then replaced by sewing in a new prosthetic vascular conduit.

Current vascular conduits are available in a variety of diameters and lengths to cater to the variations in patient anatomy, or surgeon preference. Such conduits are available as tubular structures made from woven or knit polyester yarn, PET, or also available in ePTFE. These known tubular structures have terminal ends that terminate square or flat or as a plane transverse to the centerline or longitudinal axis of the tubular structure. Consequently, during the surgical procedure, the surgeon must tailor the terminal end of the prosthetic vascular conduit with scallops, tongues or fingers to in order to approximate the aortic valve annulus (or the fringe of tissue 913 above the aortic annulus) which remains of the aortic root after the aneurysmal native sinuses of Valsalva have been resected. In cases of tricuspid aortic valves, the prosthetic graft must be fashioned with three such scallops or tongues. In the hands of inexperienced surgeons, it is challenging to fashion a graft with three such tongues, equally spaced and of similar heights and circumferential width, especially during the surgical procedure when time is of the essence, and when such conventional prosthetic aortic conduits do not have demarcation lines equally spaced apart to guide the surgeon in making three equally spaced tongues (for use in a tricuspid aortic root reconstruction) or in making two equally spaced tongues (for use in a bicuspid aortic root reconstruction).

Accordingly, there exists a need for a prosthetic vascular conduit or aortic graft with pre-shaped or pre-cut terminal ends, produced at time of fabrication of the aortic graft to avoid surgeon having to fashion such conduit ends with two tongues to mate or comply with the scalloped aortic root of a bicuspid aortic valve or with three tongues for a tricuspid aortic valve, during the course of the surgical procedure. Such a precut prosthetic graft or conduit advantageously prepared and available to the surgeon as a sterile implant in various sizes, before the surgical procedure, would greatly facilitate the implantation of the replacement aortic conduit during surgery. As well, consistency in the size and shape of the prefabricated tongues would minimize unwanted variability and tend to improve surgical outcome.

Prosthetic aortic conduits are provided sterile and in a variety of different sizes. As such, a hospital must stock the entire range of sizes available in order to cater to whatever patient anatomy presents during surgery. To exploit the benefits of a prefabricated scalloped conduit and to limit the inventory of different sizes and configurations of aortic conduits that a hospital must stock in sterile inventory, it is advantageous to have an aortic conduit having a first terminal end fashioned with two scallops or tongues in the event that a patient with a bicuspid valve presents, and a second opposed terminal end fashioned with three scallops or tongues in the event that a patient with a tricuspid valve presents. Such a conduit with two scalloped terminal ends would improve the logistics associated with stocking sterile implants, reordering and traceability of same, since fewer graft configurations must be managed within the hospital's inventory pool. A solitary graft chosen based on its tubular diameter can be selected for the surgical case, and then depending on the patient's specific anatomy of aortic valve, either the tri-scalloped or bi-scalloped end of the graft implanted to the aortic root through a proximal anastomosis, while the opposite end of the graft is cut away from the tubular portion of the conduit since it is not appropriate for that patient's anatomy. Moreover, the cutting away of the not-needed scalloped end along a length of tubular portion of the graft, prepares same for the distal anastomosis to the native ascending aorta.

It is thus a first object of the present invention to provide a prosthetic aortic conduit having a first terminal end configured and sized with three tongues to comply or mate with a scalloped tricuspid aortic root, and a second terminal end configured and sized with two tongues to comply or mate with a scalloped bicuspid aortic root.

It is a further object to provide a prosthetic aortic conduit having pre-shaped scalloped first and second terminal ends, provided sterile, in order to minimize the inventory of different graft diameter sizes to be stocked at the hospital to cater to whatever patient anatomy presents itself during the course of a surgery.

It is a further object to provide a prosthetic aortic conduit wherein said tongues have reinforced free margins along the zone where the proximal anastomosis suture line is placed between the resected native aortic root and the scalloped terminal end of the prosthetic aortic graft.

It is a further object of the present invention to provide a prosthetic aortic conduit wherein said tongues have free margins configured with sealing members or hydrogel members or improved sealing interfaces or surface treatments in order to promote or enhance the hemostasis of the suture line between the prosthetic graft and the native scalloped aortic root.

It is a further object of the present invention to provide a prosthetic aortic conduit wherein said tongues have free margins impregnated or configured with a biological or tissue glue to help promote adhesion of the prosthetic graft to the native scalloped aortic root.

It is a further object of the present invention to provide a prosthetic aortic conduit wherein said tongues have free margins treated with a pharmacological agent effective in promoting with tissue-ingrowth into the aortic prosthesis, or treated with a bioreaction controlling agent effective in controlling the pannus growth between the native and prosthetic aortic graft.

It is also a further advantage to provide a prosthetic aortic conduit for use in conservative aortic valve surgeries where the native valve cusps are preserved, but there exists the need to replace aneurysmal aortic root tissue, such as the Sinuses of Valsalva, or an aneurysmal ascending aorta with a tailored prosthetic conduit.

SUMMARY OF THE INVENTION

It is a general object of the present invention to provide such an improved vascular implant and associated surgical method for use in aortic valve-sparing procedures, or other aortic valve or aortic root reconstruction surgeries wherein a portion of the aortic root needs to be replaced, especially a portion including the sinuses of Valsalva.

BRIEF DESCRIPTION OF THE DRAWINGS

Various embodiments of the present invention will now be disclosed, by way of example, in reference to the following drawings in which.

DETAILED DESCRIPTION

Figure 14:
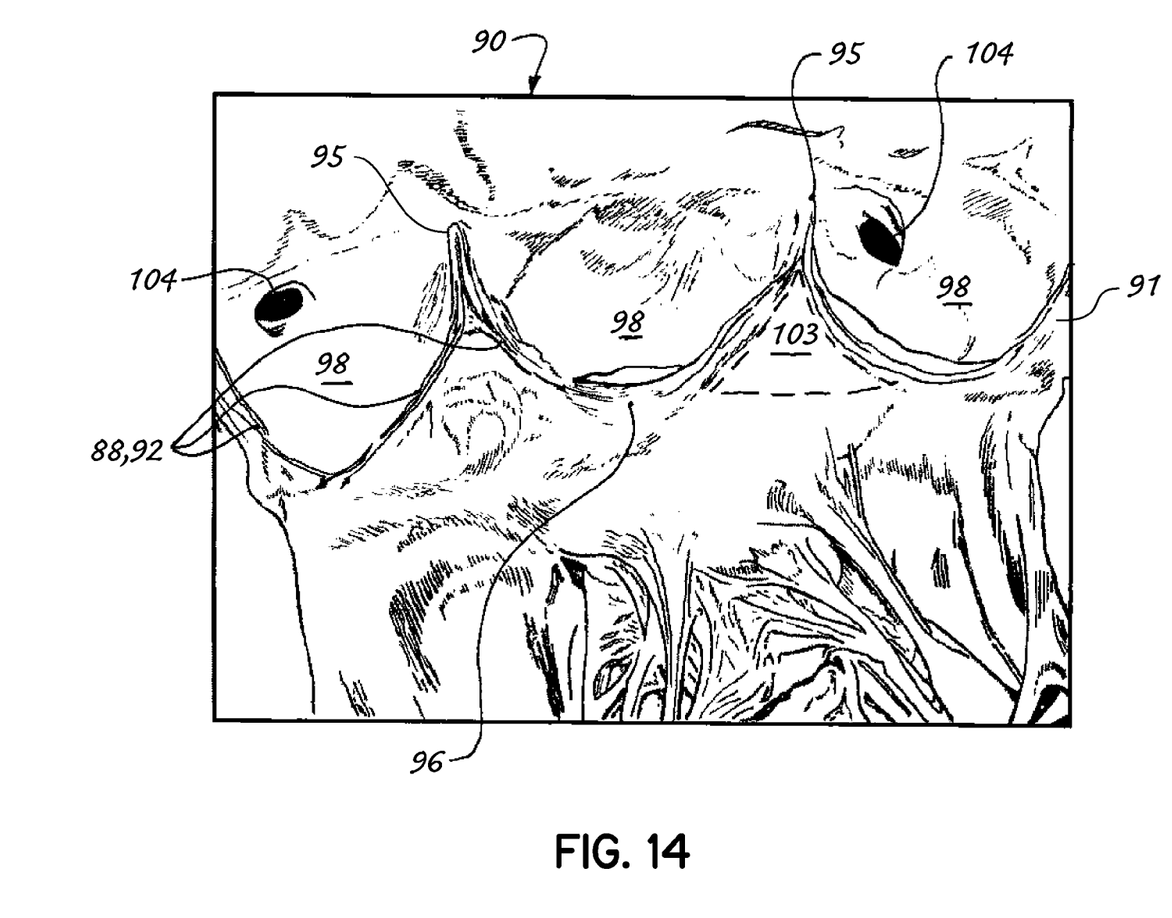
FIG. 14 is a representation of a native aortic root 90 that has been flat-wrapped to show the aortic structures of same, except for the valve cusps which are not shown.
Figure 15:
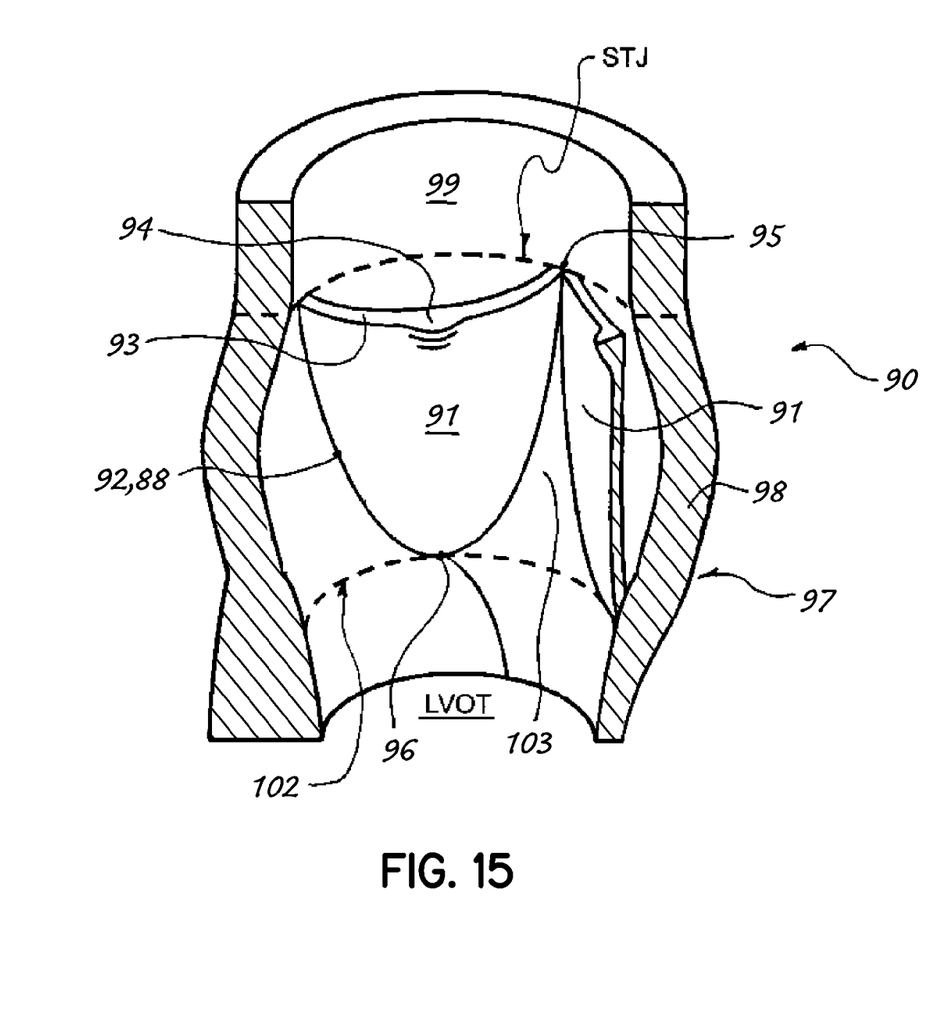
FIG. 15 is a schematic cut away view of the aortic root 90 prior to resection of the native sinuses of Valsalva.
Figure 16:
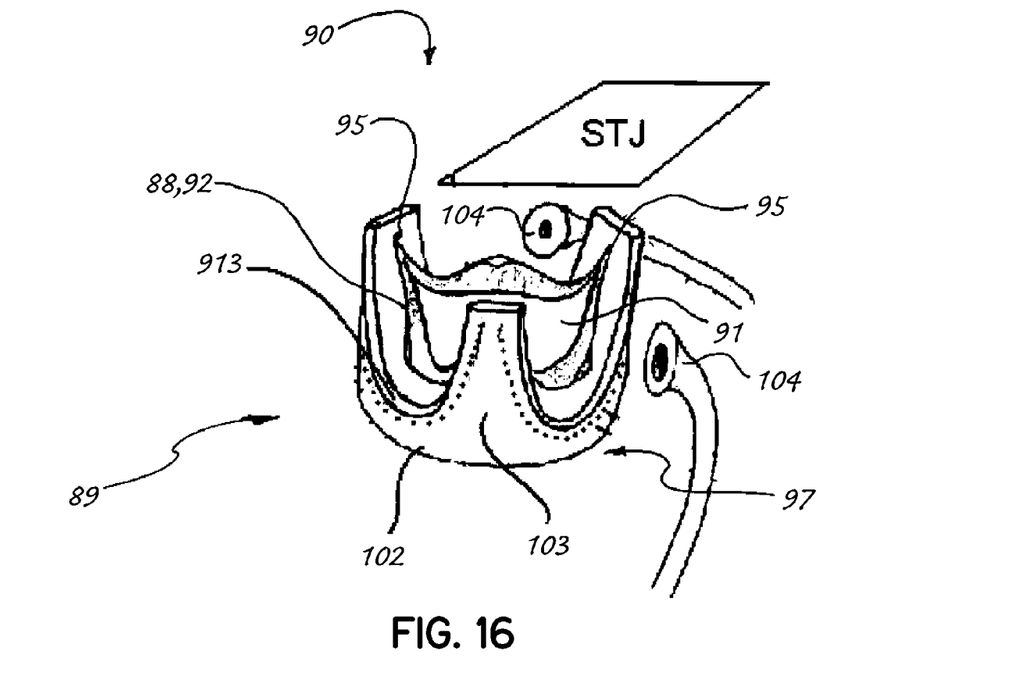
FIG. 16 is a schematic perspective view of aortic root 90 after resection of the native sinuses of Valsalva and prior to implantation of aortic conduit 1.
Figure 17:
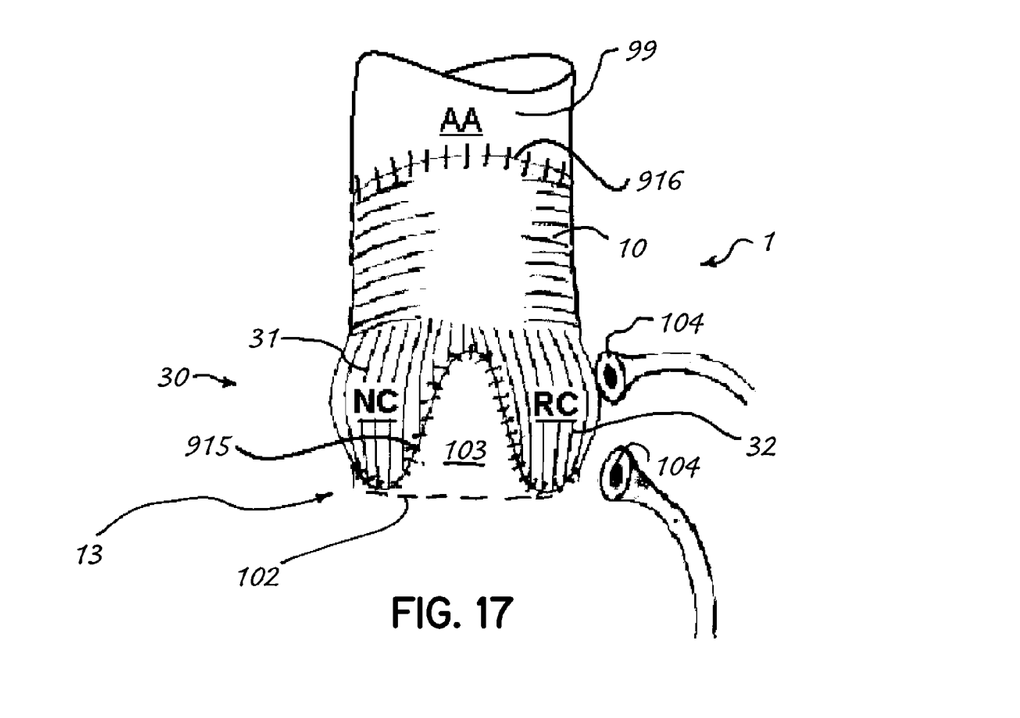
FIG. 17 is a schematic perspective view of the aortic root 90 after implantation of aortic conduit 1 and prior to reattachment of coronary ostia or buttons 104.

Referring to FIGS. 14-16, the anatomic features or aortic structures of the aortic root complex 90 will now be described in greater detail with reference to a three cusp or tricuspid aortic valve 91. Each of the valve leaflets or cusps 91 are attached at the scalloped insertion line 88 which follows the scalloped fibrous tissue referred to as the aortic valve annulus 92. The generally half-circle cusps 91 extend from said insertion line to their unattached free margin 93. The lowest insertion point of the cusp is known as the nadir 96. The diameter or plane through the three nadirs is known as the basal ring or basal diameter 102. The approximate midpoint of the free margin is characterized by a local cusp thickening known as the nodulus of Arantius 94. Free margins 93 of adjacent cusps 91 meet at the aortic wall to define commissures 95. The pouch-like bulbous portions of aortic root wall behind cusps 91 define the sinuses of Valsalva 98. The substantially triangular zone of aortic wall located below the cusp insertion line 88 of adjacent cusps and above the basal ring diameter 102 is the interleaflet triangle 103 (shown delimited by dashed lines in FIG. 14). Two of the three sinuses of Valsalva include coronary ostia 104.

In a patient presenting a tricuspid aortic valve, there are three sinuses of Valsalva and the aortic annulus is scalloped with three peaks in the vicinity of commissures 95 and three valleys in the vicinity of nadirs 96. In a patient presenting a bicuspid aortic valve, there are two sinuses of Valsalva 98 and the aortic annulus is scalloped with two peaks in vicinity of two commissures 95, and two valleys in vicinity of nadirs 96.

The anatomic features or aortic structures of the aortic root serve as landmarks or anatomic datum to guide the surgeon during aortic valve surgery or reconstructive surgery of the aortic root complex, or even replacements of a portion of the aorta that needs to be replaced.

Figure 1:
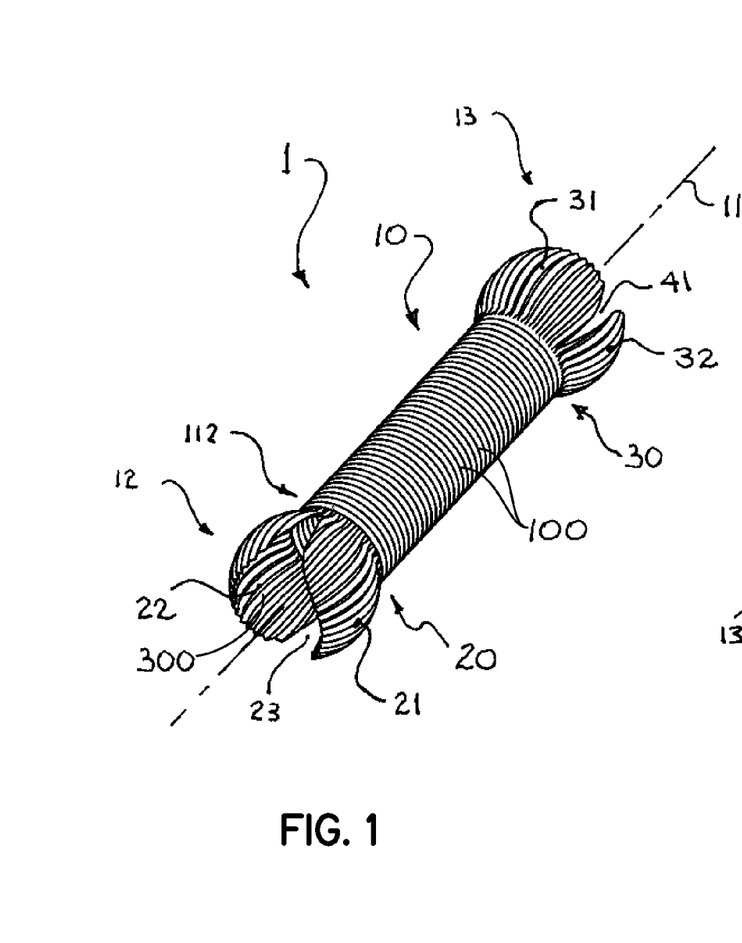
FIG. 1 in a perspective view illustrates a prosthetic aortic conduit 1 in accordance with a first preferred embodiment of the present invention for use in aortic valve surgery or aortic root reconstruction surgery.
Figure 2:
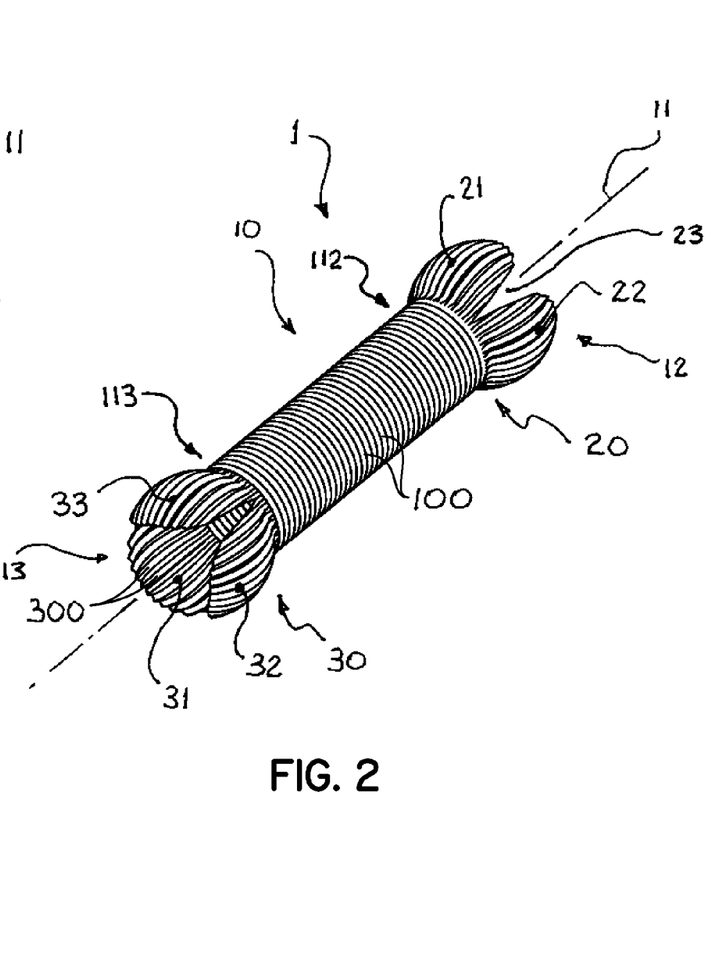
FIG. 2 is an opposite perspective view illustrating prosthetic aortic conduit 1 of FIG. 1 from an opposite side thereof.

Referring to FIGS. 1 and 2, there is shown a prosthetic vascular conduit or aortic graft or conduit 1 in accordance with a first embodiment of the present invention. Aortic conduit 1 is elongate extending along longitudinal or centerline axis 11 between a first conduit terminal end 12 and a second conduit terminal end 13. Aortic conduit 1 comprises an elongate central tubular portion or member or shell 10 extending longitudinally between a tubular first end 112 and a tubular second end 113. Tubular portion 10 is formed by a cylindrical conduit or graft surface 114 of diameter DTUBE, which as illustrated in FIGS. 1-2 is preferably crimped or pleated over a length L with an array of axially-stacked pleats or crimps 100 disposed axially along, or in the direction of, longitudinal axis 11. Tubular portion 10 has an internal diameter appropriately configured and sized to allow aortic bloodflow therethrough.

Aortic conduit 1 further comprises a bifoliate scalloped member or portion 20 attached to or extending from tubular first end 112. Scalloped portion 20 is configured with two substantially U-shaped leaf members, tongues, fingers, petals, or graft extensions 21, 22 extending away from said tubular portion 10 generally along said longitudinal axis 11. Leaf members 21, 22 are appropriately sized so as to be able to provide or create new prosthetic or neosinuses of Valsalva to replace the native sinuses of Valsalva in a bicuspid aortic root when said scalloped portion 20 is implanted to said aortic root adjacent to cusp insertion line 88 thereof.

Aortic conduit 1 further comprises a trifoliate scalloped member or portion 30 attached to or extending from tubular second end 113. Scalloped portion 30 is configured with three substantially U-shaped leaf members, tongues, fingers, petals, or graft extensions 31, 32, 33 extending away from said tubular portion 10 generally along said longitudinal axis 11. Leaf members 31, 32, 33 are appropriately sized so as to be able to provide or create new prosthetic or neosinuses of Valsalva to replace the native sinuses of Valsalva in a tricuspid aortic root when said scalloped portion 30 is implanted to said scalloped aortic root 89.

As illustrated, scalloped portions 20, 30 are provided or configured with a plurality or array of circumferentially-stacked pleats or crimps 300 disposed circumferentially about longitudinal axis 11. Said pleats 300 may provide extra volume to the neosinuses of Valsalva after said aortic conduit is implanted to aortic root.

By having an aortic conduit 10 having both terminal ends 12, 13 advantageously shaped, precut, fashioned or configured and sized with respectively a bifoliate scalloped portion 20 and trifoliate scalloped portion, the surgeon can simply select from inventory stores, and remove from the sterile package, a single aortic conduit based on a desired aortic conduit diameter (DTUBE), and have available two different ready-to-implant conduit terminal ends. This avoids the need to have a surgeon shape the terminal ends of conventional conduits while the patient is on extracorporeal circulation. In use, depending on whether the patient respectively presents a tricuspid or a bicuspid aortic valve, the aortic conduit 1 is positioned with the corresponding trifoliate 30 or bifoliate 20 scalloped portion that approximates of matches the native tricuspid or bicuspid aortic root. This selected end of the conduit will constitute the proximal implantable end. The opposite scalloped end, which is not required, is simply cut away from the aortic conduit, generally by a transverse cut through tubular portion 10, thereby also preparing said tubular portion for the distal anastomosis to the native aorta (usually the ascending aorta AA which has not be resected).

Figures 3, 4, 5, 6:
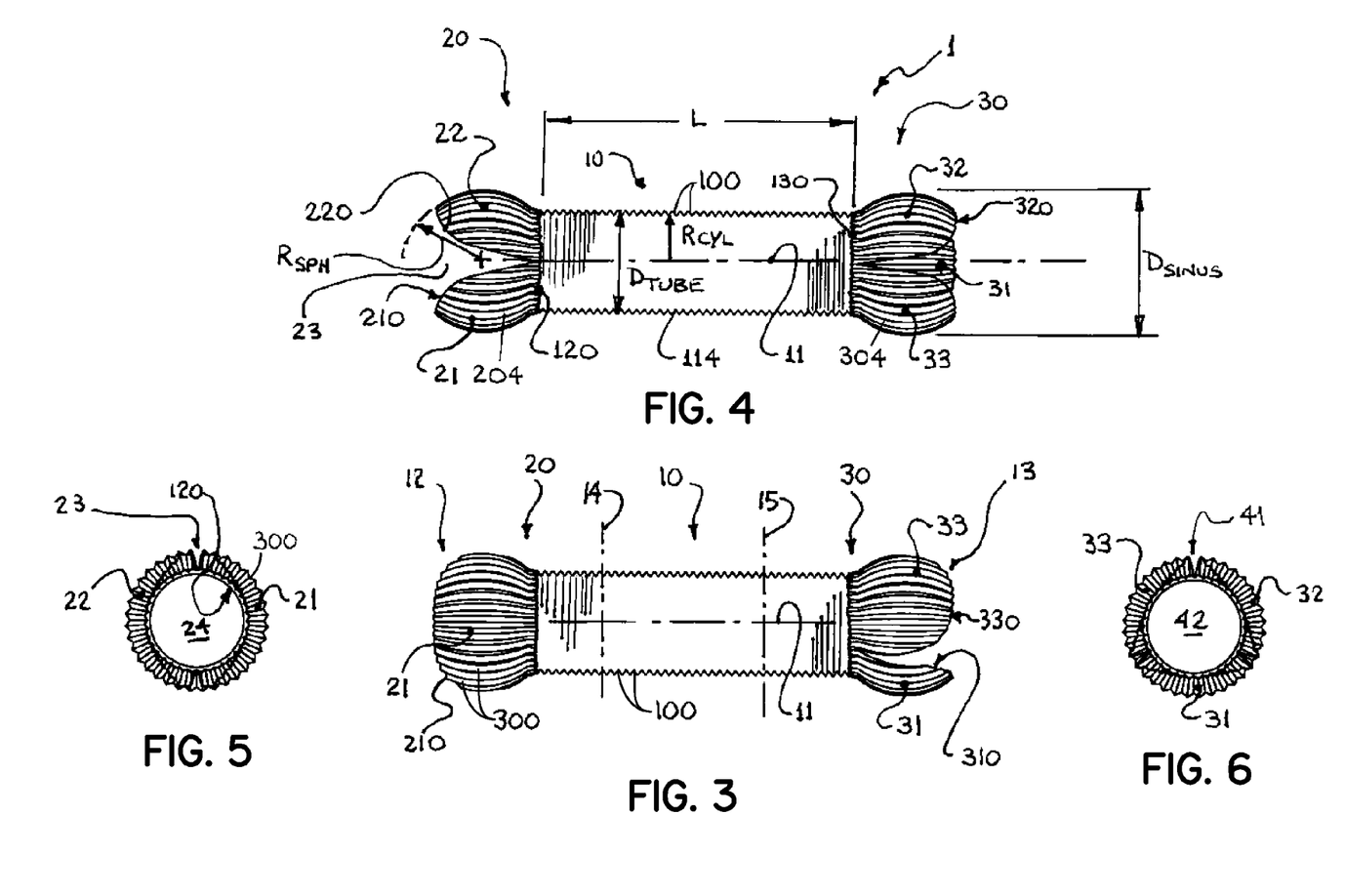
FIG. 3 is a side elevational view of aortic conduit 1 of FIG. 1.
FIG. 4 is a top view of aortic conduit 1 illustrated in FIG. 3.
FIG. 5 is a left side end view of aortic conduit 1 illustrated in FIG. 3.
FIG. 6 is a right side end view of aortic conduit 1 illustrated in FIG. 3.

Referring to FIG. 3, line 14 schematically illustrates an exemplary location along tubular portion 10 where conduit 1 may be cut to implant a portion of aortic conduit on the right side of line 14, and more particularly trifoliate or tri-scalloped end 30 to a tricuspid aortic root 90 through a proximal anastomosis. In this case, the portion of aortic conduit 1 located on the left side of line 14 (namely the bifoliate scalloped portion 20) is discarded, and the end of tubular portion 10 adjacent to line 14 is prepared for the distal anastomosis to the native aorta.

Similarly, line 15 schematically illustrates an exemplary location along tubular portion 10 where conduit 1 may be cut to implant a portion of aortic conduit on the left side of line 15, and more particularly bifoliate or bi-scalloped end 20 to a bicuspid aortic root through a proximal anastomosis. In this case, the portion of aortic conduit 1 located on the right side of line 15 (namely the trifoliate scalloped portion 30) is discarded, and the end of tubular portion 10 adjacent to line 15 is prepared for the distal anastomosis to the native aorta.

As illustrated in FIGS. 1-4, tubular portion 10 extends generally linearly along longitudinal axis 11. Alternatively, tubular portion 10 may be preformed or shaped to extend in a generally arcuate manner along a curved line of symmetry or curve 43 (as illustrated in FIG. 13D). Said curve may approximate or resemble the natural curvature of the native aortic arch. As such, the resulting variant aortic conduit 4 will have a curved tubular portion with a bifoliate scalloped portion 20 attached at a first end thereof, and trifoliate scalloped portion 30 attached at an opposed second end thereof.

Referring to FIG. 4, tubular portion 10 is generally defined by a cylindrical surface 114 of diameter DTUBE and length L. Portions 20 and 30 are generally defined by a spherical surface 204, 304 respectively of diameter DSINUS, or radius RSPH. That is, the surface defining tongues 21, 22, 31, 32, and 33 is a portion of a sphere having a radius RSPH, said portion of sphere being delimited at free end of tongue members by free margins 210, 220, 310, 320, 330, respectively, and delimited at the tongue attachment location to tubular member 10 by arcuate segment or transition boundary 120 for tongues 21, 22, and by arcuate segment or transition boundary 130 for tongues 31, 32, 33. Along transition boundaries 120, 130 adjacent tongues, petals, or fingers are in close proximity to one another, or even come into contact with one another. For example, tongue 31 is in contact with tongue 32 at transition boundary 130. After implantation of aortic conduit 1, the location where adjacent tongue members come into proximity with each other along said transition zones, will be adjacent the commissures 95 of aortic root 90. DSINUS is advantageously larger in diameter than DTUBE in order to resemble the geometry of the native aortic root. As such, the range DSINUS is approximately 1.25 to 1.5 times larger than DTUBE, and preferably in the range 1.3 to 1.4 times larger than DTUBE. Other aortic conduit variants are also possible with different geometric relationships. In other variant, DSINUS is approximately the same diameter as DTUBE, and the scalloped portions 20 and 30 are essentially extensions of the tubular portion 10 having a continuation of axially stacked crimps 100 even on said scalloped portions 20, 30.

As illustrated in FIG. 4, tubular portion 10 is of uniform diameter DTUBE. Alternatively, the diameter of tubular portion 10 may be tapered along the length L having a larger diameter at one end, for example at end 113, and a smaller diameter at for example at end 112.

The generally U-shape profiles of tongue or leaf members 21 and 22 are respectively defined by tongue free margins 210 and 220. Free margins between adjacent tongues (for example 210, 220) delimit a substantially triangular open zone 23 extending between tubular first end 112 and first conduit terminal end 12, said open zone 23 being free from conduit surface or material. Said open zones are configured to accommodate therebetween the interleaflet triangles of a bicuspid aortic root when aortic conduit 1 is implanted. In a similar manner, the generally U-shape profiles of tongue or leaf members 31, 32, and 33 are respectively defined by tongue free margins 310, 320, and 330. Free margins between adjacent tongues (for example 310, 320) delimit a substantially triangular open zone 41 extending between tubular second end 113 and second conduit terminal end 13, said open zone 41 being free from conduit surface or material. Said open zones are configured to accommodate therebetween the interleaflet triangle 103 of tricuspid aortic root 90 when aortic conduit 1 is implanted. U-shaped tongue free margins 310, 320, 330 are configured and sized to approximate the scalloped aortic annulus 92 or cusp insertion line 88. During implantation, conduit 1 will be secured to the native aortic root 90 by passing retention sutures (typically a running suture line 915) through the conduit material at said free margin location, or in proximity thereto, and also through the fringe 913 of aortic root tissue located generally above the aortic annulus 92. Fringe 913 is formed by the aortic root tissue left behind and above cusp insertion line 88, when the native sinuses of Valsalva in need of replacement have been resected from native aortic root. Having the perimeter length of the tongue free margins 310, 320, 330 similar in length to the cusp insertion line 88 facilitates suturing of the aortic conduit 1 to the scalloped aortic root 89 with evenly-spaced suture bites through both the graft and the native tissue.

The terminal ends of tongues 21, 22 are spaced apart to provide open communication 24 with tubular portion 10. Terminal ends of tongues 31, 32, 33 are spaced apart to provide open communication 42 with tubular portion 10.

Aortic conduit 1 may be provided in a variety of classified diametrical sizes DTUBE and lengths L so that he appropriate conduit can be selected and unpackaged in order to suit a specific patient anatomy or surgeon preference. Typically, aortic conduit 1 will have a length L ranging between 8 to 12 inches (20 and 30 cm). Diameters will typically range between 26 and 34 mm, and offered in classified sizes differing by 2 mm within this typical range. Other variants, outside this typical range of diameters and length are also possible, for example, to cater to paediatric patients.

Aortic conduit 1 is illustrated with pleats or crimps 100 over tubular portion 10, to prevent kinking of the graft when it is manipulated during surgery and implanted in a manner that bends the longitudinal axis 11.

Aortic conduit 1 is preferably fabricated with known biocompatible materials such as biocompatible textile material like polyester, PET. The material is preferably of a woven fabrication, but may also be knit, or non woven such as produced from fibre melt blowing or electrospinning of polyester or PET materials. Alternatively still, conduit may be fabricated from ePTFE, PTFE, or other appropriate biomaterials approved for use as aortic conduits.

Crimping 100 may be alleviated in parts of graft or conduit 1 if said conduit is preshaped with a desired predetermined bend during fabrication thereby avoiding the need to bend the straight conduit and also avoiding the likelihood of graft kinking. For example, less crimping over tubular portion 10 may be needed if instead of tubular portion extending linearly along line 11, said tubular portion is shaped to extend over an arcuate curved line with desired bend. FIG. 13D illustrates an arched graft extending over a curved line of symmetry 43 being free of crimps on arched tubular portion 110.

As illustrated in FIGS. 1-4, aortic conduit 1 is illustrated and preferably configured with equally sized tongue members 21, 22 and equally sized tongue members 31, 32, 33. Alternatively, a variant conduit may be fabricated with tongue member 21 larger in size than tongue member 22. Alternatively, scalloped end 30 may be comprised of three unequally sized tongue members, or two similarly sized tongue members and one larger tongue member to cater to variations in patient anatomies. This may be advantageous in having an aortic conduit with one tongue member larger than the other two, said larger tongue member destined for implantation in the non-coronary cusp (NC) position which is often a larger cusp than the right coronary (RC) and left coronary (LC) cusp.

Figure 7:
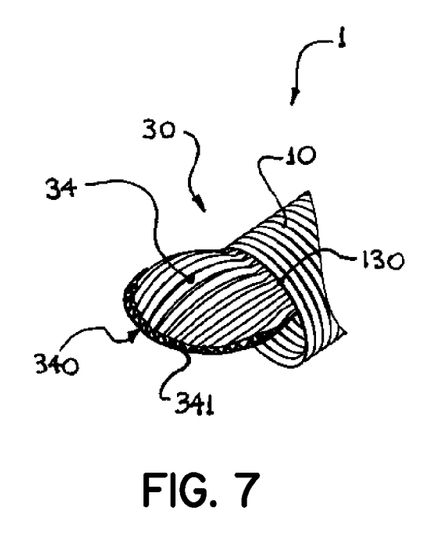
FIG. 7 is a perspective view of the first end of an aortic conduit, with two of three petals not shown, illustrating a reinforcement seam or conduit strengthening member 341 along free margin 340 of a tongue member 34.

Referring to FIG. 7, trifoliate scalloped portion 30 is configured with a variant U-shaped tongue member, petal, leaf member, or finger 34 (other two tongue members removed for clarity). Tongue member 34 is configured with a reinforcement seam or conduit strengthening member 341 along free margin 340 of a tongue member 34. Said reinforcement serves to buttress or better support the sutures that will be placed though said tongue along free margin 340 to secure conduit 1 to scalloped aortic root 89. Local reinforcement as provided by 341 allows the remainder of conduit to be sized with thinner wall section to advantageously promote tissue ingrowth while providing strength in the conduit where suture pull out may be a concern. Member 341 is appropriately configured to resist plication of free margin 340 when said free margin is sutured to fringe 913 of scalloped aortic root 89. As such, leakage of blood through plicated free margin of graft is avoided or minimized leading to a more hemostatic suture line 915.

Figure 8:
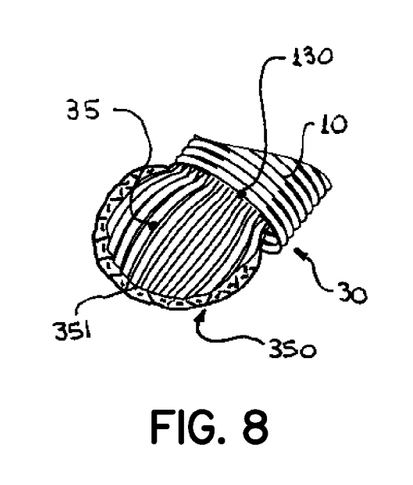
FIG. 8 is a perspective view of the first end of an aortic conduit, with two of three petals not shown, illustrating a biological glue member 351 along free margin 350 of a tongue member 35.

Referring to FIG. 8, trifoliate scalloped portion 30 is configured with a variant U-shaped tongue member, petal, leaf member, or finger 35 (other two tongue members removed for clarity). Tongue member 35 is configured with a hydrogel coating or biological tissue glue member 351 along free margin 350 of a tongue member 35. Said coating or glue member serves to reduce the likelihood of post-operative bleeding across the proximal anastomosis suture line 915 by providing an adhesion between the native tissue and prosthetic graft material in addition to the mechanical joint formed by suturing therebetween. Alternatively, member 351 can be laced with a bioreaction controlling agent to control pannus growth at the interface between native aortic root 90 and prosthetic graft material. Alternatively still, member 351 can be treated with a pharmacological agent to promote controlled tissue ingrowth at interface between native aortic root and prosthetic graft material.

Figure 9:
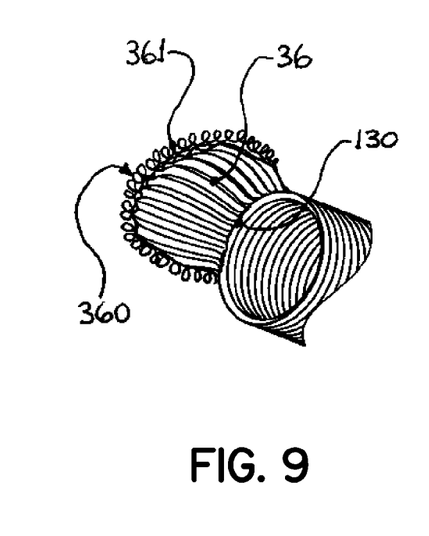
FIG. 9 is a perspective view of the first end of an aortic conduit, with two of three petals not shown, illustrating a seal member or hemostasis-promoting zone 361 along free margin 360 of a tongue member 36.

Referring to FIG. 9, trifoliate scalloped portion 30 is configured with a variant U-shaped tongue member, petal, leaf member, or finger 36 (other two tongue members removed for clarity). Tongue member 36 is configured with a seal member or hemostasis promoting zone 361 along free margin 360 of a tongue member 36. Said sealing member serves to reduce the likelihood of post-operative bleeding across the proximal anastomosis suture line 915 by providing a compliant, elastic or spongy interface between native tissue and graft material.

Figure 10:
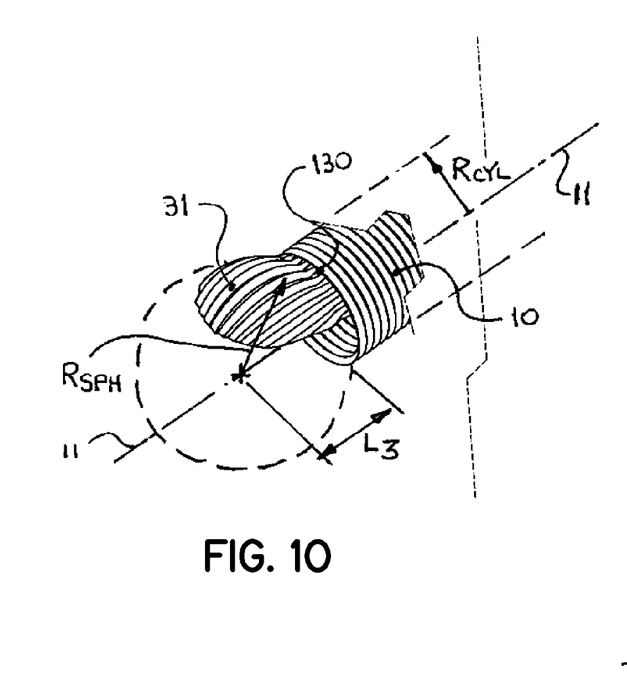
FIG. 10 is a perspective view of the first end of an aortic conduit, with two of three petals not shown, illustrating the geometric relationship of the tongue member 31 to form neosinuses relative to the tubular portion 10 of prosthetic graft 1.

Referring to FIG. 10, an exemplary configuration of a tongue member 31 is illustrated. For clarity in the illustration, tongue members 32 and 33 are not shown in this figure. Tongue 31 (and also 32, 33) are defined by spherical surface having a spherical radius RSPH. RSPH is preferably 1.25 to 1.5 times larger than DTUBE, and more preferably between 1.35 and 1.4 times larger than DTUBE. The configuration of tongues 31, 32, 33 may be set according to the above parameters either before or after crimping or pleating with pleats 300 has taken place.

Figure 11:
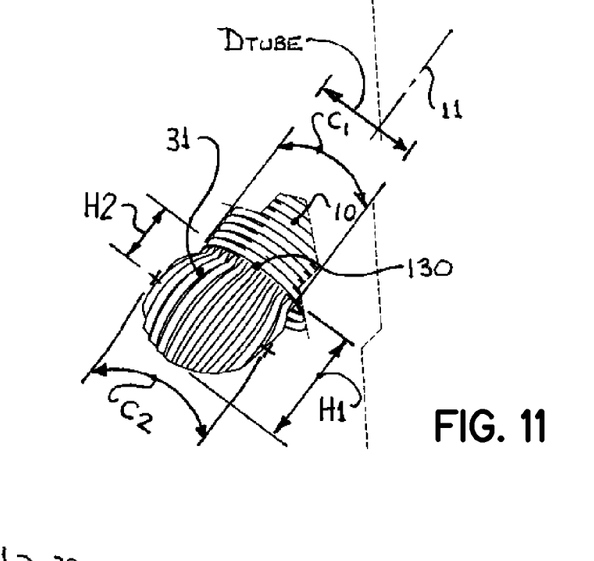
FIG. 11 is a perspective view of the first end of an aortic conduit, with two of three petals not shown, illustrating the geometry and size of a tongue member 31.

Referring to FIG. 11, an exemplary configuration of a tongue member 31 is illustrated. For clarity in the illustration, tongue members 32 and 33 are not shown in this figure. The height H1 of tongue member 31 (axial distance along axis 11 away from tubular end 13 or away from boundary 130) is preferably between 0.8 to 1.2 times the diameter DTUBE of tubular portion 10. Tongue 31 is attached to tubular portion 10 along transition boundary 130 over an arcuate length C1 representing approximately one third of the circumference of a diameter DTUBE. At approximately the mid height location of H2, tongue member 31 has an arcuate length C2. C2 is preferably 1.2 to 1.4 times larger than C1 in order to provide ample graft material or conduit surface to fashion bulbous neosinuses of Valsalva after aortic conduit 1 is implanted. After implantation, adjacent tongue members (for example 32, 31) will not come into contact with each other at this H2 location since interleaflet triangle 103 will be interspersed between adjacent tongue members at this location filling up open zone 41.

Figure 12:
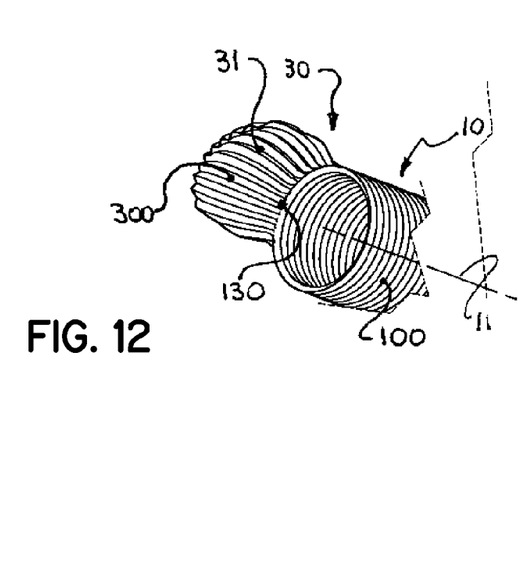
FIG. 12 is a perspective view of the first end of an aortic conduit, with two of three petals not shown, illustrating a variation in crimping or pleating between tongue member 31 and tubular portion 10 of aortic conduit 1.

Referring to FIG. 12, transition zone or boundary 130 between tongues 31, 32, 33 is a substantially planar circular perimeter, said circular perimeter being substantially perpendicular to longitudinal axis 11. Transition boundary also delineates the different pleat or crimp 300 configurations: axially stacked pleats 100 on tubular member 10, circumferentially disposed pleats over the tongue members 31, 32, 33.

Figure 13A:
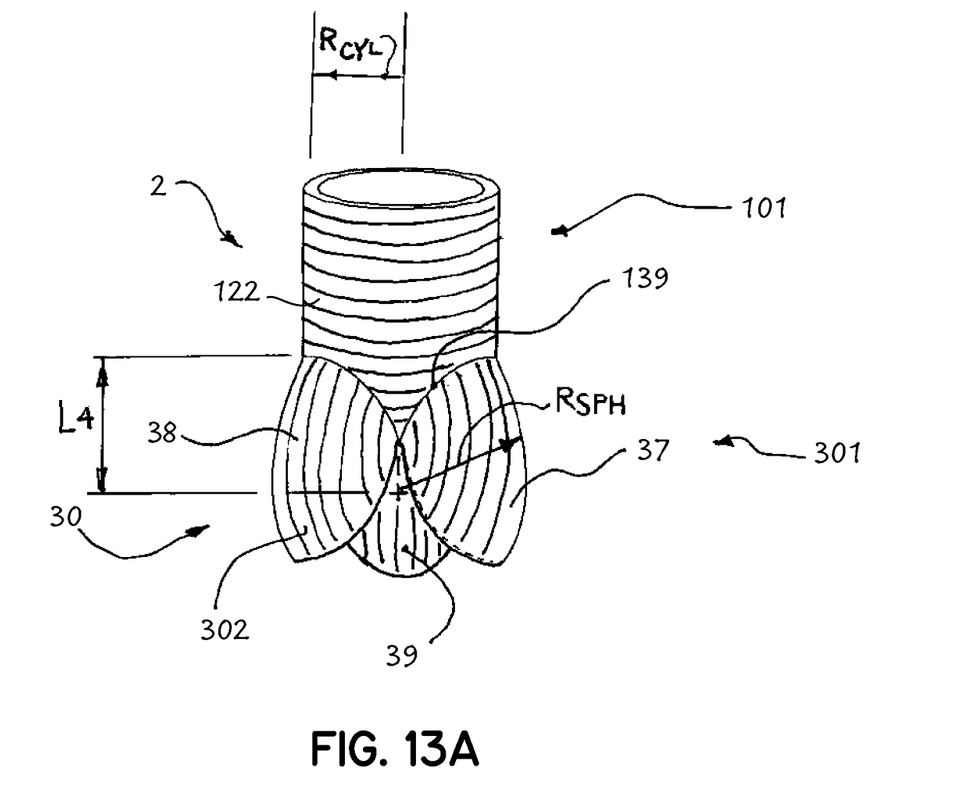
FIG. 13A is a side elevational view of a variant prosthetic conduit 2 having a variant crown shaped transition boundary 139 delimiting the tubular portion 101 having axially-stacked crimping 122 from the scalloped end 301 having circumferentially-stacked crimping 302.

FIG. 13A illustrates a variant aortic conduit 2, having a scalloped or crown shaped transition boundary or zone or curve 139. Curved boundary 139 delimits or delineates tubular portion 101 having axial crimping 122 from conduit scalloped end 301 having circumferential crimping 302 on tongue members 37, 38, 39.

Figure 13B:
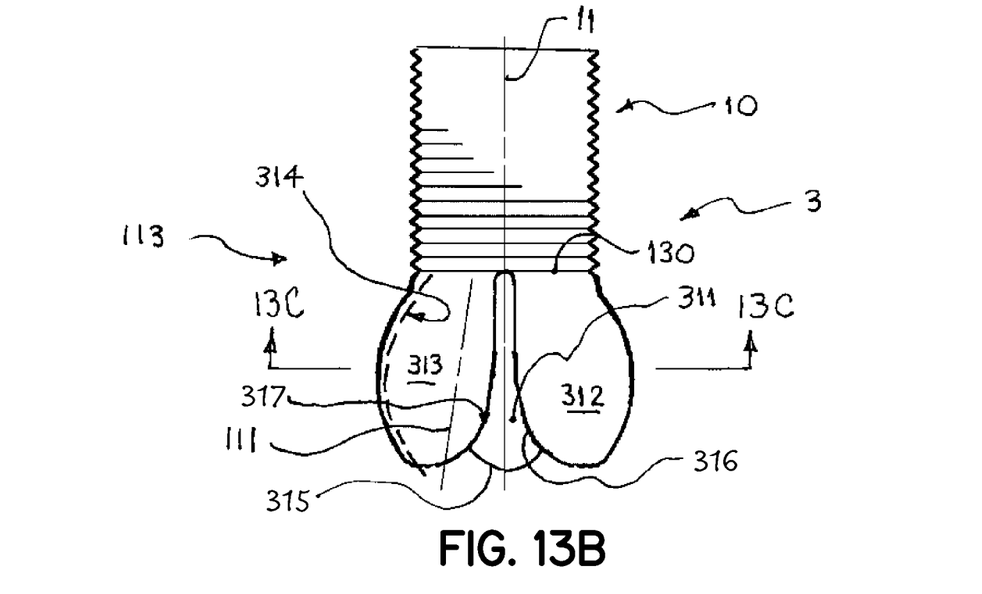
FIG. 13B is a side elevational view of a variant prosthetic conduit 3 having non-crimped tongue members 311, 312, and 313 extending from tubular second end 113, each of said tongue members being configured by sweeping curve 314 about axis of revolution 111.

FIG. 13B illustrates a variant aortic conduit 3 having non-crimped tongue members 311, 312, and 313 extending from tubular second end 113. Said non-crimped tongue members may be seamlessly woven projections extending from the tubular graft portion 10 at transition boundary 130, said projections being delimited by tongue free margins 315, 316, and 317 through the weaving process. Alternatively, conduit 3 may be woven with bulbous terminal end which is subsequently cut along free margins 315, 316, and 317 to create trifoliate scalloped end having tongue members 311, 312, 313. For instance, one method of cutting said tongues includes ultrasonic cutting which can advantageously fuse the cut edges of the woven yarn to prevent raveling.

Unlike aortic conduit 1, conduit 3 is configured with adjacent tongue members 311, 312, 313 spaced apart and not in contact with each other at transition boundary 130, in order to accommodate wider fringes 913 of aortic root tissue located in the vicinity of valve commissures 95.

Unlike aortic conduit 1, tongue members 311, 312, 313 are not defined by a common spherical surface defined by radius RSPH whose center is coincident with aortic conduit centerline 11.

Figure 13C:
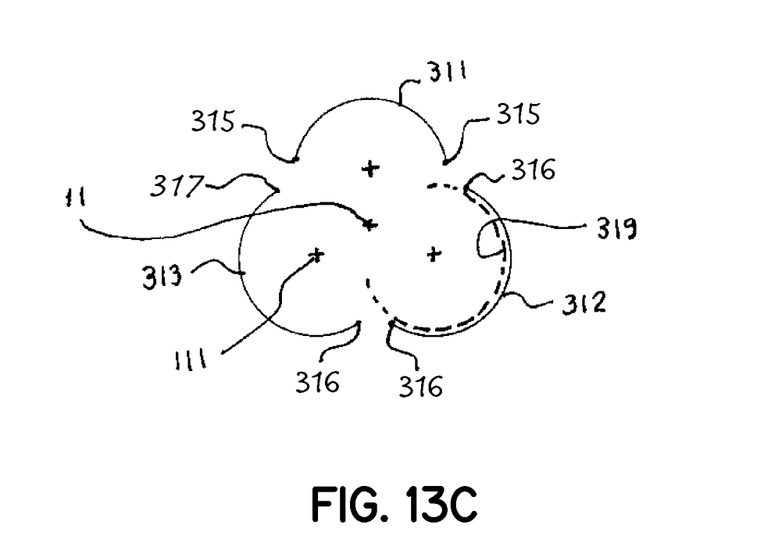
FIG. 13C is a diagrammatic cross sectional view through tongue members 311, 312, 313 of prosthetic conduit 3 illustrated in FIG. 13B.
Figure 13D:
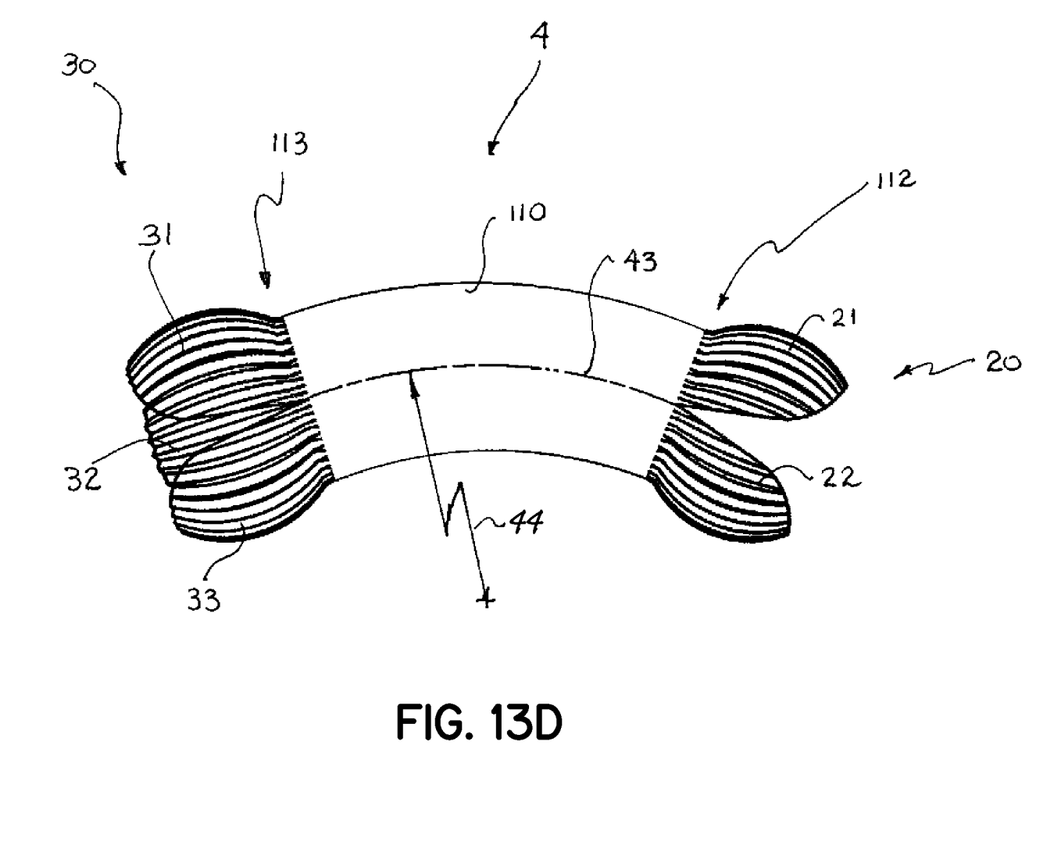
FIG. 13D is a side elevational view of a variant prosthetic conduit 4 having a variant arched tubular center portion 110 defined by a radius of curvature 44.

Referring to FIGS. 13B and 13C, each of petals 311, 312, 313 is defined by a surface of revolution 319 created when arc or curve 314 is swept around an axis of revolution 111. Preferably, axis of revolution 111 is offset radially away from graft axis 11. Preferably, axis of revolution 111 is angled relative to axis 11 and diverges away from axis 11 in direction toward graft terminal end. The position and orientation of axis 111 and the definition of arc 314 are determined in a manner that a resulting surface of revolution 319 approximates the shape of the native sinuses of Valsalva. As well, free margins 315, 316, 317 are preferably configured and sized to approximate the cusp insertion line 88 of a native aortic valve or the scalloped annulus 92 of the native aortic valve.

Referring to FIG. 13D a variant prosthetic conduit 4 is illustrated having an arched tubular center portion 110 extending in length over a curved line of symmetry 43, the latter having a radius of curvature 42. Preferably, radius of curvature 44 approximates the curvature of the native aortic arch. Arched conduit 4 may be manufactured with non-woven graft technology (i.e. fiber melt blowing or electrospinning). Fabricating said arched graft with a prefabricated bend radius 44 thereby eliminates or reduces the number of crimps placed over the arched center portion 110 since such a bent graft is less prone to kinking. As illustrated, trifoliate scalloped portion 30 and bifoliate scalloped portion 20 are configured with circumferentially stacked crimps similar to aortic conduit 1.

One example of a surgical method for use of aortic conduit 1 comprises the following steps:

Assess diameter of native aortic root 90;

Resect aneurysmal aortic tissue to produce a scalloped aortic root 89 having tissue fringe 913 extending above cusp insertion line 88;

Assess diameter of scalloped aortic root 89 and select the appropriate diameter of aortic conduit 1 needed to reconstruct the aortic root;

Determine whether native aortic valve is a bicuspid or tricuspid valve;

For bicuspid aortic valves, cut through tubular portion 10 and discard scalloped portion 30;

For tricuspid aortic valves, cut through tubular portion 10 and discard scalloped portion 20;

Implant non-discarded portion of aortic conduit by suturing either scalloped portion 20 to bicuspid aortic root, or scalloped portion 30 to tricuspid aortic root to create the proximal anastomosis 915

Create the distal anatomosis 916 by suturing tubular portion 10 to native ascending aorta AA.

The invention claimed is:

1. A prosthetic aortic conduit for use during surgery on the aorta of a patient, said aorta including an aortic root, said aortic root including either a tricuspid or bicuspid aortic valve, said tricuspid valve having a scalloped tricuspid valve annulus, said bicuspid aortic valve having a scalloped bicuspid valve annulus, said conduit comprising:
- an elongate tubular portion extending along a longitudinal axis between a first conduit terminal end and a second conduit terminal end,
- said first conduit terminal end being configured with two substantially U-shaped tongues extending away from said tubular portion generally along said longitudinal axis, each of said tongues being appropriately sized to together collectively approximate the shape of the scalloped bicuspid valve annulus;
- said second conduit terminal end being configured with three substantially U-shaped tongues extending away from said tubular portion generally along said longitudinal axis, each of said tongues being appropriately sized to together collectively approximate the shape of the scalloped tricuspid valve annulus;
- whereby, in use, either one of a corresponding said first or second conduit terminal end may be implanted to the aortic root, depending on whether the patient respectively presents a tricuspid or a bicuspid aortic valve.

2. A prosthetic aortic conduit for use during surgery on the aorta of a patient, said aorta including an aortic root, said aortic root depending on the patient's specific anatomy including either a tricuspid or bicuspid aortic valve and respectively either three or two sinuses of Valsalva, said tricuspid valve having a scalloped tricuspid valve annulus, said bicuspid aortic valve having a scalloped bicuspid valve annulus, said aortic conduit being elongate and extending along a longitudinal axis between a first conduit terminal end and a second conduit terminal end, said conduit comprising:
- an elongate central tubular portion, said tubular portion extending longitudinally between a tubular first end and a tubular second end, said central tubular portion having an internal diameter appropriately configured and sized to allow aortic bloodflow therethrough,
- a bifoliate scalloped portion, said bifoliate scalloped portion attached to said tubular first end and being configured with two substantially U-shaped leaf members extending away from said tubular portion generally along said longitudinal axis, each of said of two leaf members being appropriately sized to collectively approximate together the shape of the scalloped bicuspid valve annulus;
- a trifoliate scalloped portion, said trifoliate scalloped portion attached to said tubular second end and being configured with three substantially U-shaped leaf members extending away from said tubular portion generally along said longitudinal axis in opposite direction to said bifoliate scalloped portion, each of said of three leaf members being appropriately sized to collectively approximate together the shape of the scalloped tricuspid valve annulus;
- whereby, in use, depending on whether the patient respectively presents a tricuspid or a bicuspid aortic valve, said aortic conduit is positioned so that the corresponding said trifoliate or said bifoliate scalloped portion of said aortic conduit is surgically implanted to the patient's aortic root, in a location above the scalloped tricuspid or bicuspid valve annulus to replace respectively the three or two native sinuses of Valsalva, said tubular portion thereby replacing a portion of the aorta, and the other one of either said trifoliate or bifoliate scalloped portion not implanted to the aortic root is cut away from the aortic conduit.

\* \* \* \* \*

UNITED STATES PATENT AND TRADEMARK OFFICE
CERTIFICATE OF CORRECTION

| | |
|---|---|
| PATENT NO. | : 8,932,344 B2 |
| APPLICATION NO. | : 13/643231 |
| DATED | : January 13, 2015 |
| INVENTOR(S) | : Anthony Paolitto et al. |

It is certified that error appears in the above-identified patent and that said Letters Patent is hereby corrected as shown below:

Title Page

At (75), change "Velentini" to --Valentini--.

In the Specification

Column 2

Line 18, delete "to".

Line 36, before "surgeon" insert --the--.

Column 3

Line 39, delete "with".

Column 6

Line 20, change "of" to --or--.

Column 7

Line 23, delete the second occurrence of "at".

Line 63, change "he" to --the--.

Column 8

Line 12, change "non woven" to --non-woven--.

In the Claims

Column 12

Claim 2, line 8, delete the second occurrence of "of".

Claim 2, line 17, delete the second occurrence of "of".

Signed and Sealed this
Twenty-third Day of June, 2015

Michelle K. Lee
*Director of the United States Patent and Trademark Office*